United States Patent [19]

Jorneus et al.

[11] Patent Number: 5,741,267
[45] Date of Patent: Apr. 21, 1998

[54] DEPTH-MARKING SYSTEM ARRANGEMENT FOR IMPLANT HOLES IN THE JAWBONE

[75] Inventors: Lars Jorneus, Frillesas, Sweden; Richard Sullivan, Westmont, Ill.

[73] Assignee: Nobel Biocare AB, Goteborg, Sweden

[21] Appl. No.: 530,383

[22] PCT Filed: Feb. 10, 1995

[86] PCT No.: PCT/SE95/00137

§ 371 Date: Dec. 5, 1995

§ 102(e) Date: Dec. 5, 1995

[87] PCT Pub. No.: WO95/21590

PCT Pub. Date: Aug. 17, 1995

[30]     Foreign Application Priority Data

Feb. 14, 1994 [SE] Sweden ................................... 9400479

[51] Int. Cl.$^6$ .................................................. A61B 17/16
[52] U.S. Cl. ............................. 606/102; 606/80; 606/72; 606/73; 433/72; 433/75; 433/165
[58] Field of Search ...................... 606/79, 80, 86, 606/87, 96, 102; 433/72, 75, 76, 102, 165

[56]     References Cited

U.S. PATENT DOCUMENTS

| 5,190,548 | 3/1993 | Davis ........................................... 606/80 |
| 5,342,366 | 8/1994 | Whiteside et al. .......................... 606/86 |
| 5,354,300 | 10/1994 | Goble et al. ................................ 606/80 |

FOREIGN PATENT DOCUMENTS

WO 93/24061  12/1993  WIPO .

Primary Examiner—Michael Buiz
Assistant Examiner—David O. Reip
Attorney, Agent, or Firm—Pollock, Vande Sande & Priddy

[57]     ABSTRACT

A depth-marking system for use in connection with forming holes for receiving implants in a jawbone. The implants have a nominal length less than an actual length. At least one band marking is arranged on a tool for forming or measuring the implant holes. The at least one band marking includes a first line that indicates the actual hole depth, the actual depth including any lower cone-shaped portion of the hole. The at least one band marking also includes a second line above the first line that indicates a position of an uppermost of a unit arranged on the implant when the implant is in a final position in the hole and the unit is arranged in a final position on the implant.

18 Claims, 1 Drawing Sheet

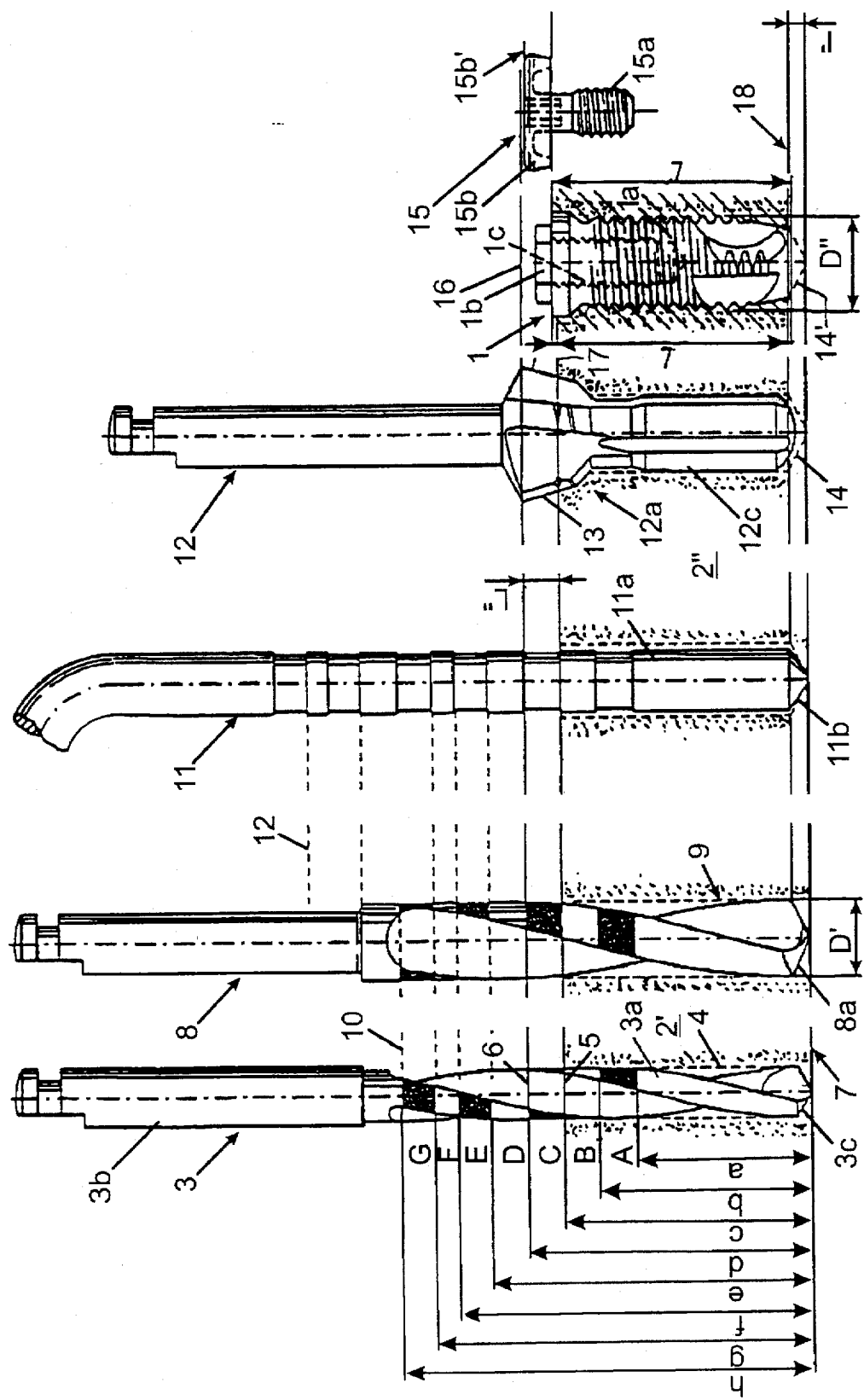

DEPTH-MARKING SYSTEM ARRANGEMENT FOR IMPLANT HOLES IN THE JAWBONE

FIELD OF THE INVENTION

The present invention relates to a depth-marking system arrangement in connection with the formation of implant holes in the jawbone. The present invention includes at least one band markings arranged on the tool being used, that is drill, countersinking drill, among others and, if appropriate, on the measuring instrument. Each implant is ascribed a nominal length that is less than the actual length of the implant.

BACKGROUND OF THE INVENTION

It is well known to form holes in the human jawbone. The drill speeds are relatively high, for example 2500 rpm. During the drilling and hole-forming work, it is known to make use of marking systems comprising bands for determining the hole depth.

SUMMARY

In connection with forming holes for implants, a need has arisen for better functioning depth-marking systems. The present invention aims to solve this problem among others.

The present invention proposes to form holes on the inner part of the jawbone. This in contrast to know methods where implant work was carried out exclusively on and in the front parts of the jawbone. The inner parts of the jawbone are rich in nerves. Therefore, greater accuracy in respect of the depth of the holes formed must be possible, to ensure that nerves are not damaged when forming the holes. It is important that the user should have accurate information relating to the varying depth of the respective hole as the work is progressing. The present invention solves this problem too.

The use of band markings which are known per se must be adapted to the high degree of accuracy of indication. It is important, in this respect, that no misjudgments should be possible on the part of the user. The present invention solves this problem too.

According to the present invention, the novel depth-marking system is employed on tools and measuring instruments used in work for forming holes. It is important that band markings be in relation to the different functions of the tools and measuring instruments. The present invention solves this problem.

Alternative uses of band markings in connection with different implant areas are additionally desirable. One particular use of the depth-marking system suits one user better than it does another user. The present invention aims to solve this problem by offering different possibilities and formats for using the depth-marking system.

The feature that can principally be regarded as characterizing an arrangement according to the invention is that a first delimiting line or marking on a first band marking represents an indication of an absolute measurement of the hole depth. The absolute measurement in question in this case also includes an inner cone-shaped portion of the hole that corresponds to the cone-shaped part of the drill. Also characteristic of the present invention is a second delimiting line or marking on the first band marking or a second band marking that represents an indication of a position or a level which is reached by an upper part or upper surface of a unit arranged on the implant in question. This unit can consist of a cover screw, cap, hood, among other structures.

In one embodiment of the present invention, the first delimiting line or marking represents a lower delimiting line or marking on the band in question. The second delimiting line or marking can be represented by an upper delimiting line or marking on the said band in question.

In further embodiments, two or more band markings can be arranged, with intermediate spacings between the band markings, on a tool in the form of one or more drills, by means of which the formation of the implant holes can be carried out. Each band marking can in this case be used for indication in conjunction with the formation of implant holes of different depths. In addition, two or more band markings can be arranged on a measuring instrument in the form of a measuring probe that can be applied in the implant hole that has been formed. Each band marking can in this case be used for indication in conjunction with the formation of implant holes of different depths.

The system also includes a countersinking tool. The countersinking tool is provided with a countersinking part, by means of which countersinking can be carried out in the upper part of the implant hole. The countersinking part is related to the spacing between the first and second delimiting lines or markings, or the width of the band, in such a way that the aforesaid spacing or width essentially corresponds to the height of the countersinking part.

The drill which is used as the tool for forming the actual hole includes a conical front part that is related to the measurement by which the nominal length of the implant is less that the actual length of the implant in such a way that the length of the conical front part essentially corresponds to the aforesaid measurement.

In a further embodiment, each marking band is assigned an implant length specific to it. The second or upper delimiting line or marking on each band can in this case represent a function measurement that is important for the user and considerably increases the clarity of indication, especially in connection with those countersinkings of the implant in the jawbone where the lower marking on the band is not so clearly seen during the work for forming the hole.

In a further embodiment, the band markings can be designed in such a way that only every second possible implant length is indicated. Each intermediate space between the depth markings forms a depth-marking band for each intermediate implant length. A particular feature in this case is that the difference between two implant lengths will be essentially the same size as the spacing between a connection plane on the upper part of the implant and the upper part of the unit/cover screw that is applied or can be applied to the implant.

By the above, it is possible to a large extent to prevent formation of bores that are too deep and may damage the nerves and nerve systems in the jaw. During the entire hole-forming operation, the user can obtain clear information on the current depth of the bore. Since the depth-marking system can be applied over a large part of the range of tools and measuring instruments, there is no need for any converting from one meaning of the indication to another meaning. Another advantage is that known band systems can be used.

BRIEF DESCRIPTION OF THE DRAWINGS

A presently proposed embodiment of an arrangement that has the characteristic features significant to the present invention will be described hereinbelow with reference to the attached drawings, in which FIG. 1 shows, in longitudinal section, an implant applied in its final position in a jawbone, FIG. 2 shows a side view of a first drill with a first diameter and with marking bands etched on the drill part, FIG. 3 shows a side view of, a second drill with a second diameter that is greater than the diameter according to FIG. 2, and with a corresponding arrangement of marking bands, FIG. 4 shows a side view of, parts of a measuring probe that is arranged with marking bands set in relation to the marking bands on the drills according to FIGS. 2 and 3.

FIG. 5 shows a side view of, a countersinking drill, in which the part carrying out the countersinking is set in relation to the relevant band on the drills according to FIGS. 2 and 3 and the measuring probe according to FIG. 4, and FIG. 6 shows a side view of, a cover screw with a cover part which is set in relation to the connection plane of the implant according to FIG. 1, and a plane which represents the top side of the relevant band.

DESCRIPTION OF THE INVENTION

FIG. 1 shows a known implant, or implant screw, 1 that is applied in a jawbone 2. The implant has a nominal length or height L which is slightly less, by a length 1, than the actual length L' of the implant. The measurement 1 can be, for example, between 0.1 and 0.2 mm. The implant 1 comprises a screw part 1a provided with an external thread, and a nut part 1b at the upper part of the implant.

FIG. 2 shows a first drill 3 with a drill part 3a and an attachment part 3b for attachment to a suitable drilling machine (not shown). Marking bands A, C, E and G are arranged on the drill part 3a. Each band, which is shown dark in FIG. 2, is assigned its own implant length. Thus, the band C is assigned the implant according to FIG. 1. The bands are arranged one above the other, with intermediate spaces B, D and F, respectively. The bands are marked by etching, mechanical marking, among other processes which can be carried out in a known manner. It is possible to regard the intermediate spaces as bands themselves, and the bands as intermediate spaces. In FIG. 2, the jawbone is indicated or symbolized by 2', and a hole formed in the jawbone by the drill 3 is partially shown by 4.

Each band has a first or lower delimiting line or delimiting marking that represents an absolute measurement of the hole depth in question. The lower line or marking, for example the line or the marking for the band C, is shown by 5. Each band also has a second or upper delimiting line or delimiting marking, which is shown by 6 in the case of band C. The absolute measurement, indicated by the band C, to the hole bottom, which is symbolized by a line 7, is shown by c in FIG. 2. The absolute measurement shown by the band A is indicated by a, the absolute measurement shown by the band E is indicated by e, and, finally, the absolute measurement shown by the band G is indicated by g. It will be seen that the bands A, C, E and G can thus be assigned to different implant lengths.

The second or upper delimiting line represents an indication of a position or a level to which, or to immediately below which, an upper part of a cover screw extends when the implant 1 according to FIG. 1 assumes its final position in the bone 2. Compare this with FIG. 6. The position or level above the bottom 7 of the hole exhibits a distance b for band A, a distance d for band C, a distance f for band E, and a distance h for band G.

FIG. 3 shows a second drill that has a construction corresponding to that of the drill 3 in FIG. 2, but having a diameter D' which is greater than the corresponding diameter of the drill 3. The drill 3 represents a preliminary drill, and the drill 8 a final drill. The drill 8 is used to form a hole 9. The implant is screwed into the wall of hole 9 tight into the bone material via the external thread of the implant. The diameter D" of the external thread of the implant the slightly exceeds the diameter D' of the drill 8. The drill 8 exhibits a marking band system corresponding to that of the drill 3. The correspondence is shown in the figure by means of horizontal lines. The upper horizontal line is designated 10.

FIG. 4 shows a measuring instrument/measuring probe. The end 11a of the probe has been provided with marking bands corresponding to those of the drills according to FIGS. 2 and 3. The correspondence is symbolized by means of horizontal lines running towards the drill 8. The upper horizontal line is shown as 12. The measuring instrument has a cone-shaped end part 11b which corresponds to the cone-shaped parts 3c and 8a of the drills 3 and 8, respectively.

FIG. 5 shows a countersinking drill 12 which has a part 12a which produces a cone-shaped portion 13 in the jawbone 2". The cone-shaped portion forms the countersunk portion. The tool 12 also comprises a guide part 12c. The lower part of the guide part can cooperate with the hole wall at the lower, cone-shaped part 14 of the hole formed by the drill. The countersinking portion 12a on the tool has a length/height L" that corresponds essentially to the width of the relevant band, that is band C in the case illustrated.

FIG. 6 shows the design of a unit in the form of a cover screw 15. Cover screw 15 includes a part 15a that has an external thread. With the external thread the cover screw can be screwed into an internal thread 1c in the implant according to FIG. 1. In addition, the cover screw has a cap-shaped part 15b that covers the nut part 1b when the cover screw is in position on the implant.

When the implant according to FIG. 1 takes up a space in the implant hole, which in FIG. 1 is symbolized by its cone-shaped part 14', an upper part or upper surface 15b' of the cap assumes a position or a level 16 which substantially coincides with, or is situated immediately below, the level of the second delimiting line or delimiting marking on the relevant band, in this case band C.

The cone-shaped part of the drill, measuring instrument and hole has a depth 1'. A connection plane for or on the implant is shown by 17. A plane 18 that marks the height 1' for the cone-shaped parts of a drill, measuring instrument, or other element, is indicated by 18.

As a result of the above, implants can be placed where the drilling depth is limited and where it is important to know exactly how deep one has drilled. In this connection it is also possible to use computed tomography in order to determine the distance from the bone surface to the nerve which is located at certain sites in the dentine. In accordance with the above, use is made of a band marking or band markings designed such that the lower edge of each band provides:

1. The absolute measurement, for example c for band C, in mm.
2. The measurement is the distance from the tip of the prepared hole to the upper connection plane 17 of the implant. Compare this to line 7.
3. The specified measurement is the normal length of the implant. For the functioning of the system, it is assumed that the implant has a nominal length L that which is somewhat shorter than the actual length (L'). This difference corresponds to the conical part that is the distance 1' of the preparing drill 3 or 8.

The upper part of each marking band, band C, for example, for a specific implant length, for example, the length of the implant according to FIG. 1, provides gives:

1. An indication of the position of the implant once the cover screw, according to FIG. 6, has been applied.
2. Furthermore, in addition to giving a function measurement, which is important for the user, this increases considerably the clarity of the indication. This is due to the face that the implant is often countersunk in the bone such that the lower marking is not so clearly seen.

In one embodiment of the present invention, it is possible, with the aid of the arrangement according to the invention, to mark only every second implant length and to let the intermediate space (B, D and F) between two colored bands (A, C or C, E or E, G) represent depth-marking bands for this intermediate implant length. In order for this embodiment to function, the difference between two implant lengths must be the same size as the distance between the connection plane 17 or the fixture and the distance to the upper part of the cover screw. Compare this to plane 16.

The invention is not limited to the embodiment shown above by way of example, but instead can be modified within the scope of the following patent claims and the inventive concept.

We claim:

1. A depth marking system for use in connection with forming holes for receiving implants in a jawbone, the implants having a nominal length less than an actual length, comprising:

at least one band marking arranged on a tool for performing at least one function selected from the group consisting of forming the implant holes and measuring the implant holes, said at least one band marking including a first line that indicates an actual hole depth, the actual hole depth including any lower cone-shaped portion of the hole, said at least one band marking also including a second line above said first line that indicates a position of an uppermost portion of a unit arranged on the implant when the implant is in a final position in the hole and the unit is arranged in a final position on the implant.

2. The depth marking system according to claim 1, further comprising a plurality of band markings on the tool, each band marking including a first line and a second line, wherein the first line and the second line of adjacent band markings overlap.

3. The depth marking system according to claim 2, wherein all of the band markings have substantially equal lengths.

4. The depth marking system according to claim 1, wherein the first line is at a lower limit of the at least one band and the second line is at the upper limit of the at least one band.

5. The depth marking system according to claim 1, wherein the unit is selected from the group consisting of a cover screw, a cap, and a hood.

6. The depth marking system according to claim 1, wherein the tool is selected from the group consisting of a drill bit, a countersinking bit, and a depth gauge.

7. The depth marking system according to claim 1, wherein the tool is a countersinking drill bit for producing a countersinking in an upper part of the implant hole, wherein a length of the countersinking portion of the countersinking drill bit essentially corresponds to a width of the at least one band.

8. The depth marking system according to claim 1, wherein the tool is a drill bit that includes a conical tip, wherein the length of the conical tip essentially corresponds to a difference between the nominal length of the implant and the actual length of the implant.

9. The depth marking system according to claim 1, wherein the at least one band corresponds to an implant length.

10. The depth marking system according to claim 1, wherein the second line facilitates a determination of depth of the hole where the first line is not easily viewed during formation of the hole.

11. The depth marking system according to claim 1, further comprising a plurality of band markings and an intermediate space between said band markings, wherein said band markings indicate every second implant length, and each intermediate space forms a depth-marking band for each intermediate implant length, a difference between two adjacent implant lengths being essentially the same size as the spacing between a connection plane on an upper part of an implant and an upper part of said unit when arranged on said implant.

12. The depth marking system according to claim 1, wherein the tool is a drill bit that includes a cone-shaped tip, and wherein a length of the cone-shaped tip substantially corresponds to the difference between the nominal size of the implant and the true length of the implant.

13. The depth marking system according to claim 1, wherein the first line indicates the nominal length of the implant and a position of a connection plane on the implant that the unit will rest upon when arranged on the implant.

14. A depth gauge system for use in forming a bore in dentine, the bore for receiving an implant, the implant being capable of receiving a covering screw having a cap, comprising:

a device for performing at least one function selected from the group consisting of forming said bore and measuring a depth of said bore;

a plurality of band markings on said device, each band marking having a first border line for indicating an absolute depth of the bore including any cone shaped portion of the bore and a second border line for indicating a level above the first border line;

wherein the implant has a nominal length that is less than the true length of the implant, and the first border line and second border line indicate levels corresponding to the level of the covering screw and the cap when the implant is in a final position in the bore and the covering screw and the cap are positioned on the implant.

15. The depth gauge system device according to claim 14, wherein the device includes a drill bit for forming the bore, the drill bit including band markings, the device also including a depth gauge that includes band markings having a height and spacing that correspond to the height and spacing of the band markings on the drill bit.

16. The depth gauge system device according to claim 14, wherein the device is a countersink drill bit including a countersink portion for forming a cone-shaped portion in an upper portion of the bore, and a distance between the first border line and the second border line substantially corresponds to a height of the countersink portion.

17. The depth gauge system device according to claim 14, wherein the device is selected from the group consisting of drill bits, countersink drill bits, and depth gauges.

18. The depth gauge system according to claim 14, wherein the tool is a drill bit that includes a cone-shaped tip, and wherein a length of the cone-shaped tip substantially corresponds to the difference between the nominal size of the implant and the true length of the implant.

* * * * *